United States Patent
Patton et al.

(10) Patent No.: US 9,418,207 B1
(45) Date of Patent: Aug. 16, 2016

(54) METHOD OF SECURELY DISTRIBUTING A CONTROLLED SUBSTANCE

(71) Applicant: Jim Patton, Edmond, OK (US)

(72) Inventors: Jim Patton, Edmond, OK (US); John Barr, Troutman, NC (US)

(73) Assignee: Jim Patton, Edmond, OK (US)

( * ) Notice: Subject to any disclaimer, the term of this patent is extended or adjusted under 35 U.S.C. 154(b) by 0 days.

(21) Appl. No.: 14/704,570

(22) Filed: May 5, 2015

(51) Int. Cl.
*G06F 19/00* (2011.01)
*A61J 7/00* (2006.01)

(52) U.S. Cl.
CPC ........... *G06F 19/3462* (2013.01); *A61J 7/0076* (2013.01); *A61J 7/0418* (2015.05); *A61J 7/0445* (2015.05); *G06F 19/3456* (2013.01)

(58) Field of Classification Search
CPC ........................ G06F 19/3462; B65D 83/0409
USPC ......................................................... 700/236
See application file for complete search history.

(56) References Cited

U.S. PATENT DOCUMENTS

| | | | |
|---|---|---|---|
| 5,347,453 A | 9/1994 | Maestre | |
| 5,408,443 A | 4/1995 | Weinberger | |
| 5,752,620 A | 5/1998 | Pearson | |
| 6,471,087 B1 * | 10/2002 | Shusterman | 221/2 |
| 7,359,765 B2 | 4/2008 | Varvarelis et al. | |
| 7,502,666 B2 | 3/2009 | Siegel et al. | |
| 7,529,597 B1 * | 5/2009 | Hertz et al. | 700/241 |
| 8,335,588 B2 | 12/2012 | Rahilly et al. | |
| 8,357,114 B2 * | 1/2013 | Poutiatine | A61J 7/0481 604/59 |

(Continued)

FOREIGN PATENT DOCUMENTS

| | | |
|---|---|---|
| WO | 2013033033 | 3/2013 |
| WO | 2013054245 | 4/2013 |
| WO | 2013127564 | 9/2013 |

OTHER PUBLICATIONS

E-Pill CompuMedMD3 Tamper Proof Pill Dispenser. Printed Oct. 25, 2013. http://www.epill.com/compumed.html. p. 1.

(Continued)

*Primary Examiner* — Timothy Waggoner
(74) *Attorney, Agent, or Firm* — Crowe & Dunleavy, P.C.

(57) ABSTRACT

A method of securely distributing a controlled substance which includes the steps of inputting a plurality of parameters into a secure pill device having a tamper resistance mechanism, shipping the secure pill device from a first facility to a second facility, periodically evaluating a first condition, comparing a first parameter in the plurality of parameters against the first condition, and engaging the tamper resistance mechanism when the first condition exceeds the first parameter in the plurality of parameters. The method may also include the steps of transferring a plurality of the controlled substance from the pill secure pill device to a patient pill dispenser having a patient tamper resistance mechanism, inputting a plurality of patient parameters into the patient pill dispenser and comparing the plurality of patient parameters with a plurality of conditions.

20 Claims, 4 Drawing Sheets

(56) References Cited

U.S. PATENT DOCUMENTS

| | | | |
|---|---|---|---|
| 8,417,378 B2 | 4/2013 | Joslyn | |
| 8,453,874 B2 | 6/2013 | Simpson et al. | |
| 8,483,872 B2 | 7/2013 | Ratnakar | |
| 8,537,004 B2 | 9/2013 | Ross | |
| 9,014,847 B2 * | 4/2015 | Dunn | 700/237 |
| 2003/0174554 A1 | 9/2003 | Dunstone et al. | |
| 2006/0058724 A1 * | 3/2006 | Handfield et al. | 700/236 |
| 2008/0179387 A1 | 7/2008 | Cantlay et al. | |
| 2010/0186923 A1 * | 7/2010 | Hu et al. | 164/513 |
| 2010/0318218 A1 * | 12/2010 | Muncy et al. | 700/237 |
| 2013/0200033 A1 | 8/2013 | Zonana et al. | |
| 2013/0248551 A1 | 9/2013 | Tignanelli et al. | |

OTHER PUBLICATIONS

E-Pill Medication Reminders. Printed Oct. 25, 2013. http://www.epill.com/drugrehab.html. p. 2.

Pill Organizer with Alarm. Printed Oct. 25, 2013. http://www.abledata.com/abledata.cfm?pageid=19327&ksectionid=19327&top=12410. p. 2.

NYPD Wants to Combat NYC Prescription Drug Theft With Device. Printed Jan. 1, 2013. http://www.huffingtonpost.com/2013/01/15/. p. 1.

* cited by examiner

METHOD OF SECURELY DISTRIBUTING A CONTROLLED SUBSTANCE

FIELD OF THE INVENTION

The present invention generally relates to the field of medication control and particularly to a method for securely distributing and preventing theft and diversion of a controlled substance.

INCORPORATION BY REFERENCE

Applicant has filed two other applications contemporaneously with this application, U.S. patent application Ser. No. 14/704,475 titled "Secure Controlled Substance Pill Dispensing Device" and U.S. patent application Ser. No. 14/704,524 titled "Secure Controlled Pill Device", each of which are hereby incorporated by reference.

BACKGROUND OF THE INVENTION

The health industry is faced with a multibillion dollar problem of prescription controlled substance theft and diversion. Unauthorized individuals sometimes impermissibly access or steal medication while it is in route from the manufacturer to the pharmacy, or remove or steal the containers after they have arrived at the pharmacy. Additionally, even when medication is properly prescribed, there can be a problem with people taking too much medication or allowing others to take the medication without authorization. Without a method of tracking or destroying medication that has been diverted from its intended route or stolen from the pharmacy, unauthorized individuals may take or sell the medication causing themselves or others harm and creating substance abuse from improper consumption of the medication. Also, without a proper device to lock the medication in the container to prevent unauthorized access, there is a danger of overdose, misuse or substance abuse. Accordingly, there is a need for a method of including anti-theft measures on a secure pill container to provide an unbroken and traceable distribution chain for delivering controlled substances from the manufacturer to the authorized receiving pharmacy. Further, there is a need for a method of securing a pill dispensing device to prevent unauthorized consumption of medication by destroying medication that has been diverted and notifying the proper authorities and that locks the container if the medication is expired. Also, there is the need for a method of including security measures on a pill container from the pharmacy to the end user to prevent overdose or diversion of the medication.

SUMMARY OF THE INVENTION

In the preferred embodiment, the present invention includes a method of securely distributing a controlled substance. The method includes inputting a plurality of parameters into a secure pill device having a tamper resistance mechanism, shipping the secure pill device from a first facility to a second facility along a preferred route and engaging the tamper resistance mechanism when one of the plurality of parameters exceeds a first condition. The method also includes a method of authenticating the second facility to allow access to the secure pill device, transferring the controlled substance from the secure pill device to a patient pill dispenser and inputting a plurality of patient parameters into the patient pill dispenser having a patient tamper resistance mechanism. The method further includes comparing the plurality of patient parameters to a plurality of conditions to determine if the controlled substance may be dispensed to the patient.

DETAILED DESCRIPTION OF THE PREFERRED EMBODIMENTS

The present invention is a system to securely distribute a controlled substance (referred to throughout as the "Secure Distribution System"). It will be understood that the Secure Distribution System is configured (or can be adapted) to distribute a variety of controlled substances. In the preferred embodiment, the controlled substance is in pill form.

Figure 1:
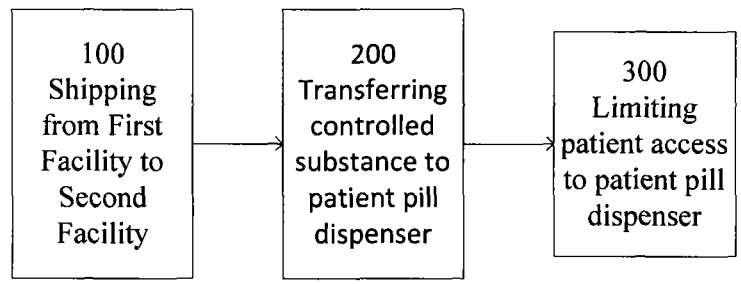
FIG. 1 is a flow chart depicting the major components of a system to securing distribute a controlled substance.

The system includes 3 principal components, each of which is depicted in FIG. 1. The first component 100 includes methods and devices that ensure the secure shipment of a controlled substance from a first facility to a second facility (depicted in FIG. 2). The second component 200 includes the methods and devices that ensure the secure transfer of the controlled substance to a patient (depicted in FIG. 3). The third component 300 includes the methods and devices necessary to secure the controlled substance after it is transferred to the patient (depicted in FIG. 3).

In the preferred embodiment, the first facility is a manufacturer of the controlled substances, such as a pharmaceutical company, and the second facility is an intermediate distribution center, such as a pharmacy. In alternate embodiments, the first facility may be a distributor, wholesaler, warehouse or other entity that desires to ship controlled substances from its facility to a second facility.

Figure 2:
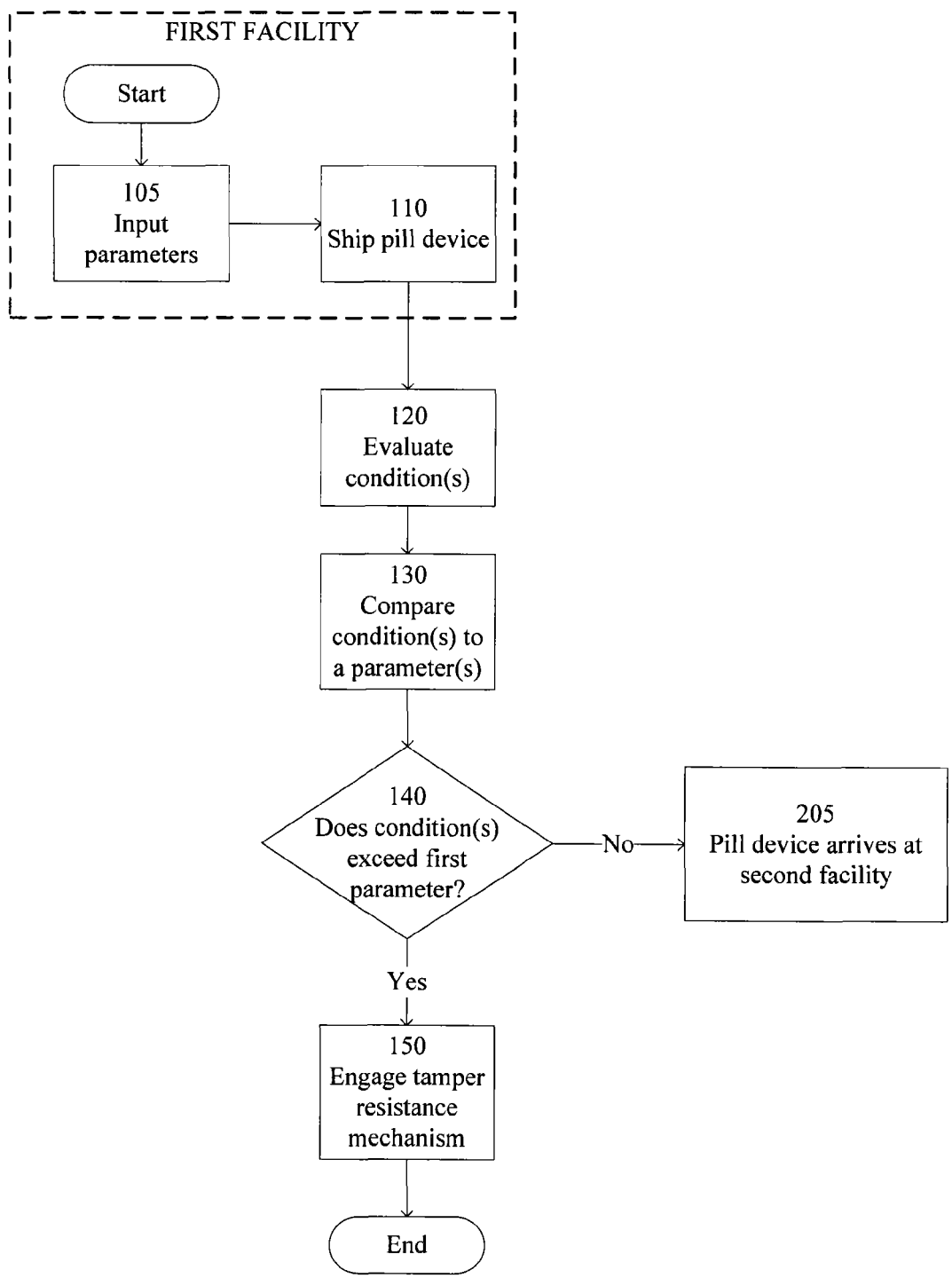
FIG. 2 is a flow chart diagram illustrating steps associated with secure distribution of the pill device from a first facility to a second facility.

Referring now to FIG. 2, depicted therein is a flow diagram illustrating the methods and devices used in first component 100. The principal device used by the first component 100, is a device for holding a plurality of a controlled substance, but preferably includes the pill devices disclosed in the applications incorporated by reference. The process of the first component 100 begins in step 105, wherein a plurality of parameters are input into the pill device. The parameters input in step 105 may include, but are not limited to, the type of controlled substance placed in the secure controlled pill device, the quantity of controlled substance included in the pill device (e.g. number of pills, tablets, gel-caps, liquid, or other substrate comprising the controlled substance), GPS coordinates of a preferred shipping route for the pill device to travel from a first facility to a second facility, GPS coordinates of the second facility, a preferred GPS fence outside which the pill device may not travel, a duration of time for the pill device to travel to the second facility, an authentication code for the second facility, and an expiration date.

After inputting the desired plurality of parameters in step 105, the process moves to step 110 wherein the pill device is shipped the first facility to the second facility. During transit from the first facility to the second facility, a first condition is evaluated in step 120. The first condition may include, but is not limited to, the current location of the pill device or the time spent en-route from the first facility to the second facility. Then, in step 130, the first condition is compared to a corresponding parameter that was input in step 105. For example, if the first condition is the current location of the pill device, the first condition might be compared to the GPS fence parameter to determine if the pill device is located outside of the GPS fence. Alternatively, the first condition might be the current time which might be compared against the duration of time allowed for the pill device to travel from the first facility to the second facility.

In an alternative embodiment of the method of the claimed invention might evaluate more than one condition in step 120 so that in step 130, the multiple conditions being evaluated could be compared to more than one of the plurality of parameters input in step 100.

The process then moves to step 140 to determine whether the first condition exceeds the first parameter. If the first condition exceeds the first parameter, the process moves to step 150 and the tamper resistance mechanism of the pill device is engaged to destroy the controlled substance located inside the pill device.

It will be understood that the determination of whether the first condition exceeds the first parameter will depend upon the particular condition and particular parameter. For example, if the first condition is the current location of the pill device, and the first parameter is the GPS coordinates of a preferred shipping route for the pill device to travel from a first facility to a second facility, then the first condition will exceed the first parameter if the current location is outside of the preferred shipping route defined by the GPS coordinates of the first parameter. As another example, if the first condition is the current time, and the first parameter is the duration of time allowed for the pill device to travel from the first facility to the second facility, then the first condition will exceed the first parameter if the time between the current time and the shipping time is greater than duration of time allowed for the pill device to travel from the first facility to the second facility. If the first condition does not exceed the first parameter, the process moves to step 205 and the pill device arrives at the second facility.

Figure 3:
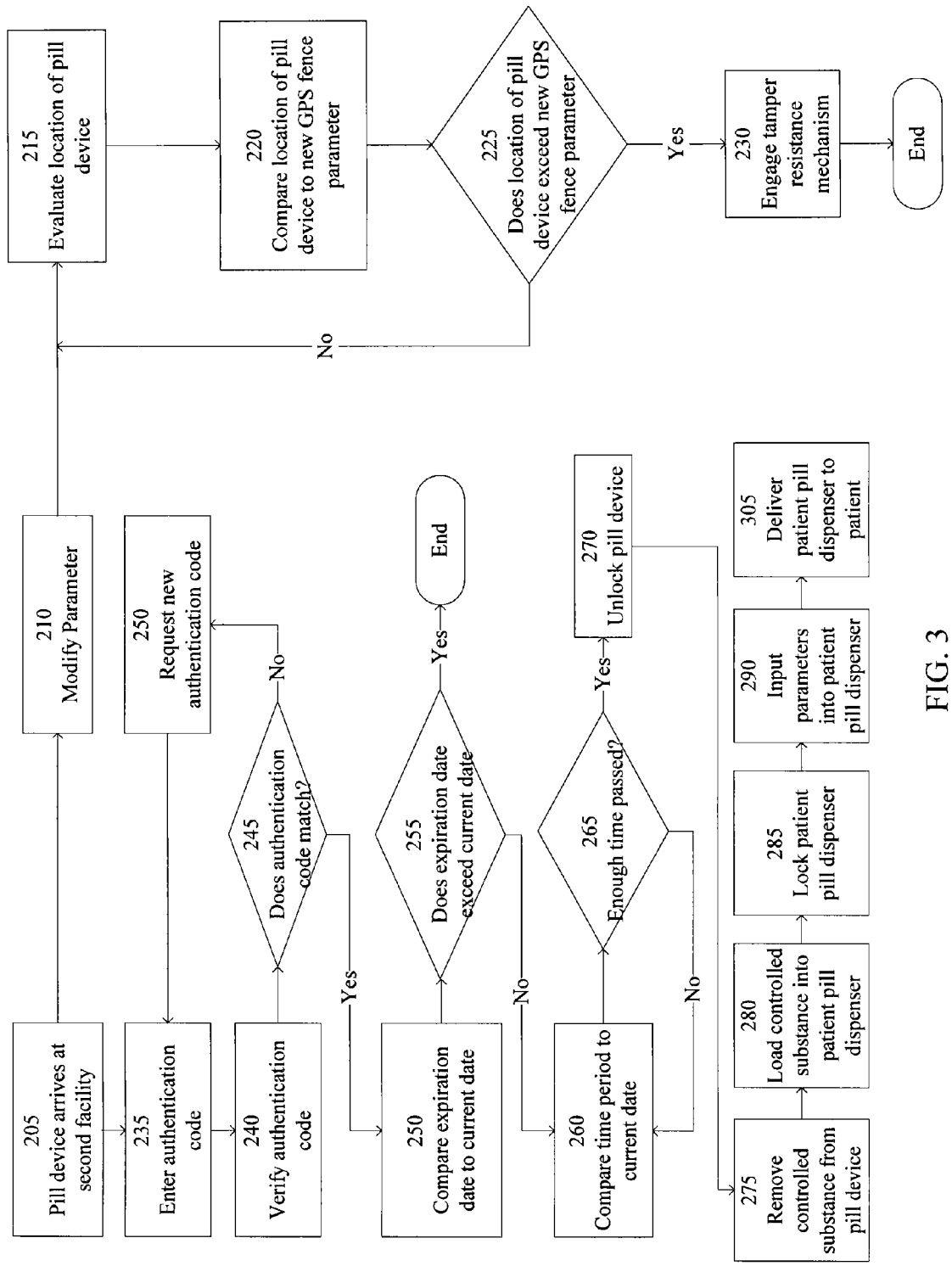
FIG. 3 is a flow chart diagram illustrating steps associated with secure distribution of a pill device and a patient pill dispenser from a second facility to the patient.

Now turning to FIG. 3, depicted therein is a flow chart diagram illustrating the methods and devices associated with the second component 200. The process in the second component 200 is concerned with securing the pill device after it arrives at the second facility and allowing the pill device to be accessed to remove and transfer a plurality of the controlled substance from the pill device to a secure patient pill dispenser.

After the pill device arrives at the second facility in step 205, a parameter in the plurality of parameters is modified in step 210. In a preferred embodiment, the parameter is a GPS fence, which is modified to a new GPS fence which is a desired distance surrounding the second facility. After the parameter is modified in step 210, the process initiates a sub-process defined by steps 215, 220, 225 and 230. This sub-process will run so long as the pill device is in use, and runs in parallel to the other methods in the second component 200.

The sub-process begins in step 215 wherein the location of the pill device is periodically evaluated and then compared to the new GPS fence parameter (from step 210) in step 220. If the location of the pill device exceeds the new GPS fence parameter, the process moves to step 230 wherein the tamper resistance mechanism is engaged to destroy the controlled substance located within the pill device. If the location of the pill device is within the new GPS fence parameter, the process continues to periodically evaluate the location of the pill device with step 215.

Also depicted in FIG. 2, is step 235, wherein an authentication code is entered into the pill device. Next, in step 240, the authentication code is verified by comparing the entered authentication code with an authentication code that was input as one of the plurality of parameters at the first facility in step 110 (See FIG. 2).

In step 245, the process determines whether the authentication code entered into the pill device in step 235 matches the authentication code entered at the first facility in step 110. If the authentication code does not match, a new authentication code is requested for input in step 250. The authentication code may be sent and/or requested from the first facility to/by the second facility via secure encryption, via email, text, or any other appropriate method. It will be understood that while the loop defined by steps 235, 240, 245 and 250 is shown to run until the authentication code matches in step 245, an alternative embodiment will only permit a desired number of loops before engaging the tamper resistance mechanism. In yet another preferred embodiment, once the desired number of loops occur, a waiting period is enacted wherein step 235 will not accept any new authentication codes until a desired time period has passed.

If the authentication code matches, the process moves to step 250 wherein the process compares the current date to an expiration date that was input as one of the plurality of parameters at the first facility in step 110. Then, in step 255, the process determines whether the expiration date exceeds the current date. If so, the process ends, maintaining the security of the pill device and preventing access by the second facility to the controlled substance within the pill device. If the expiration date does not exceed the current date, the process moves to step 260.

In step 260, the current date is compared to a time period which was input as one of the plurality of parameters at the first facility in step 110. The time period may be a time period in which the second facility is allowed to access and unlock the pill device, e.g., a set period of one week. Then, in step 265, the process determines whether enough time has passed in which the second facility is authorized to access/unlock the pill device. If not enough time has passed, the pill device remains locked and the process moves back to step 260. If enough time has passed, the pill device is unlocked in step 270.

It will be understood that steps, 240 through 265 may occur in various sequences and may not all be required. These steps are based on the plurality of parameters input in step 110 at the first facility and are optional parameters. For example, if there is no expiration date set for the controlled substance, this parameter will not be compared to a current date in step 250, but the process would instead move directly to step 260.

After the pill device is unlocked in step 270, the process moves to step 275, wherein the controlled substance is removed from the pill device. Then, in step 280, at least a portion of the controlled substance is loaded into a patient pill dispenser. The patient pill dispenser may be any type of device for holding a plurality of a controlled substance for a patient, but preferably includes the pill dispensing device disclosed in the patent applications incorporated by reference herein.

In step 285, the patient pill dispenser is locked, and then in step 290, a plurality of parameters is input into the patient pill dispenser. The plurality of patient parameters input in step 290 may include, but is not limited to, the quantity of the controlled substance loaded into the patient pill dispenser, the contact information for the pharmacy, an authorization code for the patient, and an amount of time between which the controlled substance may be dispensed to the patient. Next, the patient pill dispenser is delivered to the patient in step 305.

Figure 4:
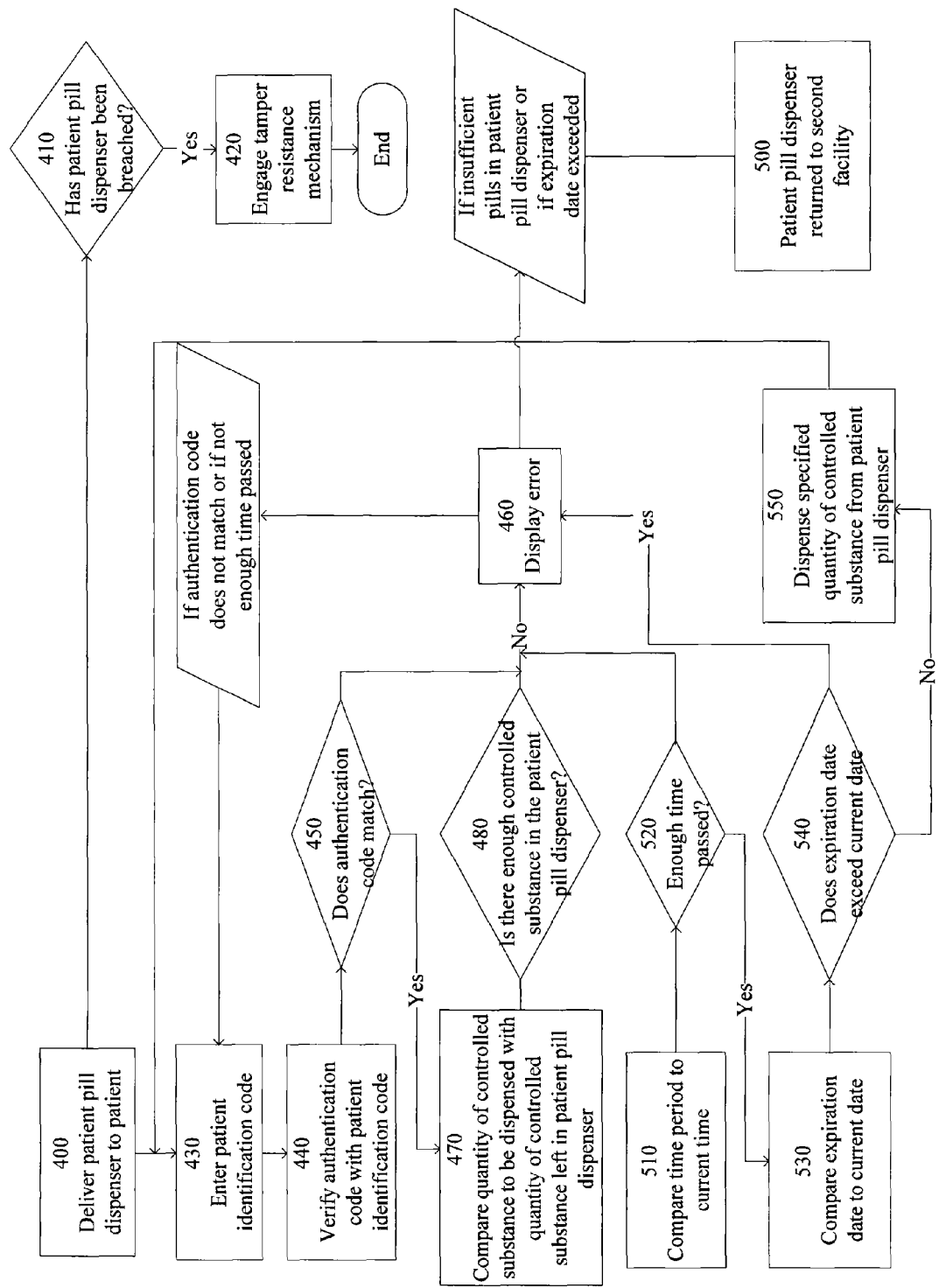
FIG. 4 is a flow chart diagram illustrating steps associated with providing limited access and theft of the patient pill dispenser.

Referring now to FIG. 4, after the patient pill dispenser has been delivered to the patient, the process in the third component initiates a parallel sub-process defined by steps 410 and 420. That sub-process is initiated if the pill dispenser device determines in step 410 whether the patient pill dispenser has been breached. If the patient pill dispenser has been breached, the process engages the patient tamper resistance mechanism in step 420 to render the controlled substance located inside the patient pill dispenser unusable.

In step 430, the patient enters a patient identification code, which is verified in step 440 with an authentication code that was entered as one of the plurality of patient parameters in step 290. Then, in step 450, the process determines whether the patient identification code matches the authentication code. If the codes do not match, the patient pill dispenser displays an error in step 460. The process then returns to step 430 to allow the patient to enter a different identification code. If the codes match in step 450, the process moves to step 470 wherein a quantity of controlled substance left in the patient pill dispenser is compared to the total quantity that was entered as one of the plurality of patient parameters in step 290.

Then in step 480, the process determines whether there is sufficient controlled substance left inside the patient pill dispenser to dispense a specified quantity of pills to the patient. If there are not sufficient pills, the process again displays an error in step 460. The process then moves to step 490 wherein the patient pill dispenser is returned to the second facility (i.e., the pharmacy) to be refilled, reused or destroyed.

If there is a sufficient quantity of controlled substance left inside the patient pill dispenser, the process moves to step 500 and compares the current time to the time period entered as one of the plurality of patient parameters in step 290. The time period entered may include a time period in which the patient may dispense a specified quantity of the controlled substance, i.e., once every 4 hours. In step 510, the process determines whether enough time has passed. If not enough time has passed, the process displays an error in step 460 and the patient must wait until sufficient time has passed and re-enter an authentication code in step 430.

If enough time has passed, the process moves to step 530 wherein the current date is compared to an expiration date that was entered as one of the plurality of patient parameters input in step 290. In step 540, the process determines whether the expiration date exceeds the current date and if so, an error is displayed in step 460. The patient pill dispenser can then be returned to the second facility in step 500 to allow refill, reuse or destruction of the patient pill dispenser If the process determines the expiration date is not exceeded by the current date the process moves to step 550 and a specified quantity of the controlled substance is dispensed from the patient pill dispenser. The process then restarts at step 430 to allow subsequent dispensing of the controlled substance from the patient pill dispenser. It will be understood that steps, 430 through 550 may occur in various sequences and may not all be required. These steps are based on the plurality of parameters input in step 290 at the second facility and are optional parameters. For example, if there is no expiration date set for the controlled substance, this parameter will not be compared to a current date in step 530, but the process would instead move directly to step 550, or alternatively, step 430.

It is clear that the present invention is well adapted to carry out its objectives and attain the ends and advantages mentioned above as well as those inherent therein. While presently preferred embodiments of the invention have been described in varying detail for purposes of disclosure, it will be understood that numerous changes may be made which will readily suggest themselves to those skilled in the art and which are encompassed within the spirit of the invention disclosed, as defined in the written description and appended claims.

The invention claimed is:

1. A method of securely distributing a plurality of pills, comprising the steps of:
 inputting a plurality of parameters into a secure pill device containing the plurality of pills and having a tamper resistance mechanism capable of rendering the plurality of pills unusable;
 shipping the secure pill device from a first facility to a second facility;
 sending a second facility identification code from the first facility to the second facility through secure encryption;
 periodically evaluating a first condition;
 comparing a first parameter in the plurality of parameters against the first condition;
 engaging the tamper resistance mechanism when the first condition exceeds the first parameter in the plurality of parameters;
 comparing an authentication code with a second facility identification code;
 unlocking the pill device if the authentication code matches the second facility identification code;
 removing a plurality of pills from the secure pill device; and
 relocking the secure pill device.

2. The method of claim 1 wherein if the authentication code does not match the second facility identification code, a different second facility identification code is requested from the first facility.

3. A method of securely distributing a plurality of pills, comprising the steps of:
 inputting a plurality of parameters into a secure pill device containing the plurality of pills and having a tamper resistance mechanism capable of rendering the plurality of pills unusable;
 shipping the secure pill device from a first facility to a second facility;
 periodically evaluating a first condition;
 comparing a first parameter in the plurality of parameters against the first condition; and
 engaging the tamper resistance mechanism when the first condition exceeds the first parameter in the plurality of parameters;
 comparing a plurality of pill device conditions with the plurality of parameters;
 unlocking the pill device if the plurality of pill device conditions meets a requirement of at least one of the plurality of parameters;
 removing a plurality of pills from the secure pill device;
 relocking the secure pill device;
 loading the plurality of pills removed from the secure pill device into a secure patient pill dispenser having a patient tamper resistance mechanism capable of rendering the plurality of pills unusable;
 inputting a plurality of patient parameters into the secure patient pill dispenser;
 periodically evaluating a second condition;
 comparing a first patient parameter in a plurality of patient parameters against the second condition;

delivering the secure patient pill dispenser from the second facility to a patient; and engaging the patient tamper resistance mechanism when the second condition exceeds the first patient parameter in the plurality of patient parameters.

4. The method of claim 3 further comprising the additional steps of:

comparing the plurality of patient pill dispenser conditions with the plurality of patient parameters; and dispensing a specified quantity of the plurality of pills to the patient if the plurality of patient pill dispenser conditions meets a requirement of at least one of the plurality of patient parameters.

5. The method of claim 3 wherein one of the plurality of patient parameters is a patient authentication code, one of the plurality of patient pill dispenser conditions is a patient identification code, and the requirement is that the patient authentication code matches the patient identification code.

6. The method of claim 3 wherein one of the plurality of patient parameters is a specified quantity of the plurality of pills in the patient pill dispenser that may be dispensed to the patient, one of the plurality of patient pill dispenser conditions is the quantity left in the patient pill dispenser, and the requirement is that the quantity left in the patient pill dispenser exceeds the specified quantity to be dispensed to the patient.

7. The method of claim 3 wherein one of the plurality of patient parameters is a specified time period in which a specified quantity of the plurality of pills in the patient pill dispenser may be dispensed to the patient, one of the plurality of patient pill dispenser conditions is the current time, and the requirement is the time elapsed prior to the current time meets the specified time period.

8. The method of claim 3 further comprising the steps of:

comparing a plurality of patient pill dispenser conditions with the plurality of patient parameters; and displaying an error code if the plurality of patient pill dispenser conditions does not meet a requirement of at least one of the plurality of patient parameters.

9. The method of claim 8 wherein the error code displayed is that the patient identification code does not match the patient authentication code.

10. The method of claim 8 wherein the error code displayed is that the plurality of pills is expired.

11. The method of claim 8 wherein the error code displayed is that the not enough time has passed to allow the specified quantity of the plurality of pills to be dispensed.

12. A method of securely distributing a plurality of pills, comprising the steps of:

inputting a plurality of parameters into a secure pill device containing the plurality of pills and having a tamper resistance mechanism capable of rendering the plurality of pills unusable;

shipping the secure pill device from a first facility to a second facility;

periodically evaluating a first condition;

comparing a first parameter in the plurality of parameters against the first condition; and engaging the tamper resistance mechanism when the first condition exceeds the first parameter in the plurality of parameters;

comparing a plurality of pill device conditions with the plurality of parameters;

unlocking the pill device if the plurality of pill device conditions meets a requirement of at least one of the plurality of parameters;

removing a plurality of pills from the secure pill device; and relocking the secure pill device;

loading the plurality of the pills removed from the secure pill device into a secure patient pill dispenser having a plurality of conditions;

inputting a plurality of patient parameters into the secure patient pill dispenser; and delivering the secure patient pill dispenser from the second facility to a patient.

13. The method of claim 12 further comprising the additional steps of:

comparing a plurality of patient pill dispenser conditions with the plurality of patient parameters; and dispensing a specified quantity of the plurality of pills to the patient if the plurality of patient pill dispenser conditions meets a requirement of at least one of the plurality of patient parameters.

14. The method of claim 12 wherein one of the plurality of patient parameters is a patient authentication code, one of the plurality of patient pill dispenser conditions is a patient identification code, and the requirement is that the patient authentication code matches the patient identification code.

15. The method of claim 12 wherein one of the plurality of patient parameters is a specified quantity of the plurality of pills in the patient pill dispenser that may be dispensed to the patient, one of the plurality of patient pill dispenser conditions is the quantity left in the patient pill dispenser, and the requirement is that the quantity left in the patient pill dispenser exceeds the specified quantity to be dispensed to the patient.

16. The method of claim 12 wherein one of the plurality of patient parameters is a specified time period in which a specified quantity of the plurality of pills in the patient pill dispenser may be dispensed to the patient, one of the plurality of patient pill dispenser conditions is the current time, and the requirement is the time elapsed until the current time meets the specified time period.

17. The method of claim 12 further comprising the steps of:

comparing a plurality of patient pill dispenser conditions with the plurality of patient parameters; and displaying an error code if the plurality of patient pill dispenser conditions does not meet a requirement of at least one of the plurality of patient parameters.

18. The method of claim 17 wherein the error code displayed is that the patient identification code does not match the patient authentication code.

19. The method of claim 17 wherein the error code displayed is that the plurality of pills is expired.

20. The method of claim 17 wherein the error code displayed is that the not enough time has passed to allow the specified quantity of the plurality of pills to be dispensed.

* * * * *